US00PP12555P2

(12) United States Plant Patent

Slaughter et al.

(10) Patent No.: US PP12,555 P2

(45) Date of Patent: Apr. 16, 2002

(54) NECTARINE TREE NAMED 'BURNECTWO'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/461,675

(22) Filed: Dec. 14, 1999

(51) Int. Cl.[7] ..... A01H 5/00

(52) U.S. Cl. ..... Plt./190

(58) Field of Search ..... Plt./190

*Primary Examiner*—Bruce R. Campell
*Assistant Examiner*—Susan B. McCormick
(74) *Attorney, Agent, or Firm*—Wells, St. John, Roberts, Gregory & Matkin, P.S.

(57) ABSTRACT

A new and distinctive variety of nectarine tree denominated varietally as 'Burnectwo' and which is characterized as to novelty by date of maturity for commercial harvesting and shipment of approximately July 1 to July 8 under the ecological conditions prevailing in the San Joaquin Valley of Central California.

1 Drawing Sheet

BACKGROUND OF THE NEW VARIETY

The present invention relates to a new, novel and distinct variety of nectarine tree, which has been denominated varietally as 'Burnetwo'. The 'Burnectwo' Nectarine Tree produces an exceptionally high quality, clingstone nectarine which is ripe for harvesting and shipment approximately in midseason. Still further, another unique aspect of the 'Burnectwo' is that it yields a firm nectarine that exhibits a very high eating quality as compared with the other nectarine varieties which ripen at approximately the same time of the season.

ORIGIN

The present variety nectarine tree was derived from an ongoing program of fruit and nut tree breeding. The purpose of this program is to improve the commercial quality of deciduous fruit and nut varieties and rootstocks by creating and releasing selections of prunus, malus and regia species. To this end, we make both controlled and hybrid crosses each year in order to produce seedling populations from which improved progenies are evaluated and selected.

The seedling 'Burnectwo' was originated by us in 1994, and chosen from among a population of seedlings which resulted from a controlled cross of the 'Grand Diamond' Nectarine Tree (U.S. Plant Pat. No. 4,095) which was used as the pollen parent, and the 'Flameglo' Nectarine Tree (U.S. Plant Pat. No. 8,441), which was used as the seed parent. The resulting seed from this cross was planted in the spring of 1995. The new variety was selected from among the seedlings then growing in experimental orchards which are located near the city of Fowler, Calif., County of Fresno, in the Central San Joaquin Valley. The 'Burnectwo' Nectarine Tree was subsequently marked and noted as having exceptional characteristics. It has been consecutively evaluated and observed during the 1996–1999 fruiting seasons. After the 1996 season, the 'Burnectwo' Nectarine Tree was selected for advanced evaluation and repropagation.

ASEXUAL REPRODUCTION

Scionwood from the original seedling of the Nectarine Tree, 'Burnectwo' was collected and grafted in the evaluation plot of the experimental orchards previously described onto two different and existing 'Nemared' (unpatented) rootstocks in February of 1997. Fruit from the resulting propagation has been consecutively evaluated and observed for each the 1998 and 1999 fruiting seasons. This subsequent evaluation clearly demonstrated that the repropagated trees are true to the characteristics of the original seedling in all observable aspects.

SUMMARY OF THE NEW VARIETY

The 'Burnectwo' Nectarine Tree is characterized as to novelty by producing fruit which has a mid-season ripening date, and which is further of very high quality, firm, and has an attractive exterior coloration. In this regard, the present variety of nectarine tree bears clingstone fruit which are ripe for commercial harvesting and shipment approximately July 1 to July 8. These harvesting dates are the same as the common commercial freestone variety 'Summer Grand' Nectarine Tree (U.S. Plant Pat. No. 2,879). The present variety of nectarine tree distinguishes itself from the 'Summer Grand' Nectarine tree by producing fruit having a brighter and more extensive exterior coloration, exceptional firmness, clingstone nature and extremely flavorful and juicy flesh quality. Further, the 'Burnectwo' Nectarine Tree distinguishes itself from the 'Summer Grand' Nectarine Tree in that the fruit of the 'Summer Grand' Nectarine Tree has a flesh color which is generally a pale-yellow hue, while the fruit of the 'Burnectwo' Nectarine Tree has a flesh color which is yellow-orange to orange, and exhibits a substantial degree of internal reddening (bleeding). The Nectarine Tree 'Burnectwo' also has a slightly higher level of acidity detected in the flavor of the flesh when compared to the more mild taste of the 'Summer Grand'. The subject variety also differs from the 'Grand Diamond' in that 'Burnectwo' is a clingstone and has much more luster in its external finish than does 'Grand Diamond'. The subject variety also differs from the 'Flameglo' nectarine in that the 'Burnectwo' fruit is generally larger in size and does not have a predominate pistil point which consistently appears on the fruit of the 'Flameglo'.

BRIEF DESCRIPTION OF THE DRAWING

The accompanying drawing is a color photograph of a characteristic twig bearing typical leaves; several leaves showing both the dorsal and ventral coloration thereof; and several mature fruit showing their external coloration sufficiently matured for harvesting and shipment. Additionally, one fruit of the subject variety is dissected in the equatorial or cheek plane to illustrate the flesh and stone characteristics.

DETAILED DESCRIPTION

Referring more specifically to the pomological details of this new and distinct variety of nectarine tree, the following has been observed under the ecological conditions prevailing near the town of Fowler, county of Fresno, state of California. All major color code designations are by reference to The R.H.S. Colour Chart (1995 Third Edition) provided by The Royal Horticultural Society of Great Britain.

Tree:

*Size.*—Generally — Average to above average as compared to other common nectarine cultivars.

*Productivity.*—Productivity with respect to pounds per acre is not available and is dependent upon cultural practices.

*Figure.*—The original seedling was trained in a central leader configuration with a moderate spread in the crown of the tree. The tree is considered upright to upright spreading in form.

*Height.*—The original seedling has a height dimension of 13.5 feet (4.1 m) at the end of the 1999 growing season.

*Width.*—The original seedling tree had a 7.2 ft. width (2.19 m) at the end of the 1999 growing season.

*Current season growth.*—The current season growth for the new variety was approximately 3.1 to 3.5 feet (0.94–1.06 m).

*Regularity of bearing.*—Regular, and considered hardy under tyical Central San Joaquin Valley conditions.

Trunk:

*Diameter.*—Approximately 2.61 inches (66.3 mm) in diameter when measured at a distance of approximately six inches (15.24 cm) above the soil level, at the end of the 1999 growing season.

*Bark texture.*—Considered moderately rough with numerous folds of papery scarf skin being present.

*Lenticels.*—Numerous flat, oval lenticels are present. The lenticels range in size from approximately 3.0 to 7.0 millimeters in width and from approximately 1 to 2 millimeters in height.

*Lenticels.*—Color — Greyed Orange Group 173 D.

*Bark coloration.*—Variable, but it is generally considered to be a grey-brown (RHS Greyed Orange Group 174 A).

Branches:

*Size.*—Considered medium for the variety.

*Diameter.*—The branches have a diameter of 38.0 mm when measured during the 3$^{rd}$ year following grafting.

*Surface texture.*—Average, and appearing furrowed on wood which is several years old.

*Current season shoots.*—Surface Texture — Substantially glabrous.

*Internode length.*—Approximately 2.3 to 2.5 cm.

*Color of mature branches.*—Medium brown, (RHS Greyed Orange Group 175 C to 177 B).

*Crotch angles.*—Variable between about 43° to 48° from the horizontal axis for scaffold limbs. This is not distinctive of the variety, however.

*Current season shoots.*—Color — Light green, (RHS Yellow Green Group 144 C), with some reddish-brown coloration appearing on exposed exterior shoots (RHS Greyed Red Group 181 B). The color of the new shoot tips is considered a bright and shiny green (RHS Green Group 143 B).

Leaves:

*Size.*—Considered average for the species. Leaf measurements have been taken from vigorous upright current season growth at approximately midshoot.

*Leaf length.*—Approximately 150 to 155 millimeters.

*Leaf width.*—Approximately 43 to 46 millimeters.

*Leaf thickness.*—Approximately 1 to 2 millimeters.

*Base shape.*—Slightly oblique.

*Leaf form.*—Lanceolate.

*Leaf tip form.*—Acuminate.

*Leaf color.*—Dark green, (RHS Green Group 132 C).

*Leaf texture.*—Glabrous.

*Lower surface.*—Light green, (RHS Yellow Green Group 146 D).

*Venation.*—Pinnately net veined.

*Mid-vein.*—Color — Light yellow green, (RHS Yellow Green Group 153 B).

*Leaf margins.*—Form — Considerate crenate, occasionally doubly crenate. Uniformity — Considered generally uniform.

*Leaf petioles.*—Size — Considered medium. Length — Approximately 9 to 12 millimeters. Diameter — Approximately 1.5 to 2 millimeters. Color — Pale green, (RHS Yellow Green Group 150 C).

*Leaf glands.*—Size — Approximately one to two millimeters in height and two to three millimeters in width. Numbers — Generally 2–3 per side, occasionally one per side. Type — Tight, small reniform. Color — Greenish brown, RHS Grey Brown 199 C.

*Leaf stipules.*—Size — Approximately 8.0 mm in length; 1.0 mm in width. Number — Typically 2 per leaf bud and up to 6 per shoot tip. Length — Approximately 6 to 10 millimeters. Form — Lanceolate in form with a serrated margin. Color — Green (RHS Green Group 132 B) when young but eventually changing to a yellow-brown (RHS Greyed Orange Group 177 B) color with advancing senescence. The stipules are considered to be early deciduous.

Flowers:

*Flower buds.*—Generally — The floral buds are considered to be medium in size (15.0 mm long and 10.0 mm wide); conic in form; and moderately free relative to the bearing shoot.

*Flower buds.*—Color — The bud scales are gray-brown, (approximately RHS Greyed Orange Group 177 B). The buds are considered hardy under typical central San Joaquin Valley climatic conditions.

*Blooming type.*—Considered average to slightly later than average in relation to other nectarine cultivars commonly growing in the central San Joaquin Valley. Approximate date of bud burst was observed on Mar. 2, 1999 and lasted approximately 8 days. Date of full bloom was Mar. 4, 1999.

*Flower type.*—The variety is considered to be a showy type flower.

*Flower diameter.*—Flower diameter at full bloom is approximately 38 to 44 millimeters.

*Bloom quantity.*—Considered abundant.

*Flower bud frequency.*—Normally 1 to 2 buds appear per node, although 1 bud per node is more common.

*Petal size.*—Generally — Considered medium-large for the species. Length — Approximately 17 to 19 millimeters. Width — Approximately 15 to 18 millimeters.

*Petal form.*—Broadly ovate.

*Petal count.*—Nearly always 5.

*Petal texture.*—Glaborous.

*Petal color.*—Light pink when young (approximately RHS Red Purple Group 69 A), and darkening with advancing senescence to a medium pink (RHS Red Purple Group 67 B). The lower portion of the flower petal is typically darker than the apical portions and exhibits a dark pink coloration (RHS Red Purple Group 64 B).

*Fragrance.*—Slight.

*Petal claw.*—Form — The claw is considered truncate in shape and has a medium size when compared to other similar varieties. Length — Approximately 1.5 to 2.1 millimeters. Width — Approximately 1 millimeter.

*Petal margins.*—Generally — The edge of the margin surface is smooth, but the plane of the margin is considered variable, to moderately undulate.

*Petal apex.*—Generally — The petal apices appear slightly domed.

*Flower pedicel.*— Length — Considered medium-short, and having an average length of approximately 2.0 to 3.0 millimeters. Diameter — Considered average, approximately 2 millimeters. Color — Bright green (RHS Yellow Green Group 144 D).

*Floral nectaries.*—Color — Dull orange, to an orange-gold color (approximately RHS Greyed Orange Group 168 B). The color of the nectaries become more dull and slightly darker with advancing senescence.

*Calyx.*—Surface Texture — Generally glabrous and having a slight ribbing. Color — A dull red, (approximately RHS Greyed Purple Group 184 A).

*Sepals.*—Surface Texture — The surface has a medium length, wooly, and gray (RHS Greyed Purple Group 183D) colored pubescence. Number — Generally 5 per flower. Size — Average, and ovate in form. Typically 4.0 mm wide and 6.0 mm long. Color — A dull red, (approximately RHS Greyed Red Group 178 A).

*Anthers.*—Generally — Average in size. Color — Red to reddish-orange dorsally, (approximately RHS Greyed Purple Group 187 D). Pollen Production — Pollen is abundant, and has a yellow-gold color, (approximately RHS Orange 26 A).

*Filaments.*—Size — Variable in length, approximately 14 to 16 millimeters. Color — Pink, (RHS Red Purple Group 68 B), and darkening with advanced maturity (to RHS Red Purple Group 67 B).

*Pistil.*—Generally — Average in size. Length — Approximately 15 to 17 millimeters, including the ovary. Color — Considered a very pale green, at mid-bloom, (approximately RHS Yellow Green Group 151 D), and becoming slightly more yellowish with advancing senescence. Surface Texture — Glabrous.

Fruit:

*Maturity when described.*—The present variety of fruit is described, as it would be found in its firm ripe condition at full commercial maturity. In this regard, the fruit of the present variety was first picked on approximately Jul. 1, 1998. The date of last pick of the same fruit in 1998 was approximately July 8 under the ecological conditions prevailing in the San Joaquin Valley of central California.

*Size.*—Generally — Large and considered moderately uniform. Average Cheek Diameter — Approximately 78 to 80 millimeters. Average Suture Diameter — Approximately 73 to 77 millimeters. Average Axial Diameter — Approximately 76 to 78 millimeters.

*Fruit weight.*—This characteristic is highly dependent on cultural practices and therefore is not distinctive of the present variety.

*Fruit form.*—Generally — Globose in its lateral aspect. The fruit is generally uniform in symmetry and having a rounded form when viewed from the apical aspect.

*Fruit suture.*—Generally — The suture appears as a thin line which extends from the base to the apex, and which appears slightly deeper, basally, within the stem well, and apically on both sides of the pistil point. No apparent callousing or stitching appears evident along the suture line.

*Suture.*—Color — The suture normally is the same color as the underlying blush, both where the orange-yellow background color (RHS Orange Group 24 C) and the red orange color, (RHS Red Group 46 A), occur.

*Ventral surface.*—Form — Considered uniform.

*Stem cavity.*—Size — Considered moderate for the species. Width — Approximately 19–22 millimeters. Length — Approximately 29–31 millimeters. Depth — Approximately 10 to 11 millimeters. Form — Considered narrrowly oval.

*Fruit base.*—Generally — Considered truncate to slightly oblique in form, and uniform.

*Fruit apex.*—Generally — Considered depressed and usually recessed below the height of the apical shoulders and often slightly oblique to the suture.

*Fruit stem.*—Generally — Considered medium in length, approximately 9 to 11 millimeters.

*Diameter.*—Approximately 3 to 4 millimeters.

*Color.*—Generally a pale yellow-green, (approximately RHS Yellow Green Group 145 B).

*Fruit skin.*—Generally — Considered average in thickness. Surface Texture — The variety has a very glabrous surface. Skin Acidity — Considered neutral.

*Tenacious to flesh.*—Yes at commercial maturity.

*Tendency to crack.*—Not observed.

*Skin color.*—Generally — Variable, with approximately 80% to 90% of the fruit surface covered with a brilliant crimson red blush.

*Blush color.*—The blush color is generally more prevalent apically. This red blush color ranges from a dark red, (RHS Red Group 46 A), to an orange red, (RHS Orange Red Group 33 B), with many degrees of shading and blending between these colorations.

*Skin ground color.*—This is generally present in variable percentages covering approximately 10% to 20% of the fruit's surface. The skin ground color is a yellow-golden color, (RHS Yellow Orange Group 22 A to 24 C).

*Flesh color.*—Generally — Considered variable, from yellow-orange, (RHS Yellow Orange Group 21 C to 21 A), to a reddish orange color, (approximately RHS Red Group 42 B), can radiate into the flesh generally beginning at the exterior margin.

*Flesh fibers.*—Generally — Present, numerous, fine and light colored. These fibers are present throughout the flesh.

*Stone cavity.*—Color — Red, (approximately RHS Red Group 45 B) to a yellow orange, (approximately RHS Yellow Orange Group 18 B). With increasing maturity, occasional red flecks can appear randomly in the flesh. These flecks are numerous and distributed throughout the pit cavity.

*Flesh texture.*—Generally — The flesh is considered firm and fine at commercial maturity. The flesh texture is considered non-melting.

*Ripening.*—Generally — The fruit of the present variety ripens evenly.

*Flavor.*— Considered very sweet, and having moderate acidity. The flavor is considered both pleasant and balanced.

*Aroma.*—Pleasant and abundant.

*Eating quality.*—Generally — Considered very good to excellent and well above average when compared to older common varieties.

Stone:

*Attachment.*—Generally — The stone is considered a true clingstone at full commercial maturity.

*Stone size.*—Generally — Considered medium to medium large for the species.

*Length.*—Approximately 32 to 35 millimeters.

*Width.*—Approximately 24 to 27 millimeters.

*Thickness.*—Approximately 23 to 25 millimeters.

*Fibers.*—Generally — A few medium length fibers are attached alone the entire surface of the stone.

*Stone form.*—Generally — The stone is considered oval to nearly elliptical in its axial aspect.

*Stone base.*—The stone base is somewhat oblique.

*Base angle.*—The base angle of the stone is variable, but most frequently is considered slightly oblique to the stone axis.

*Hilum.*—Generally — Considered medium in size, and relatively well defined. The hilum is approximately 5 to 7 millimeters long and approximately 3 to 4 millimeters wide. Form — Considered oval.

*Apex.*—Shape — The stone apex is raised and has an acute tip.

*Stone shape.*—Considered variable. The stone is normally unequal, although occasionally it may appear nearly equal.

*Stone surface.*—Surface Texture — Generally, considered medium in roughness and further exhibits substantial pitting laterally. Substantial grooving is apparent over the apical shoulders. Surface pitting is prominent, generally, and is more frequently present basally. Ridges — Numerous fine ridges are present basally and converge towards the base of the stone.

*Ventral edge.*—Width — Considered medium, and having a dimension of approximately 5 to 7 millimeters at mid-suture. Wings are most prominent over the basal area.

*Dorsal edge.*—Full, heavily grooved and having jagged edges. The dorsal edge is moderately eroded over the apical shoulder.

*Stone color.*—The color of the dry stone is approximately a light to medium brown, (RHS Orange Red Group 34 C).

*Tendency to split.*—No splitting noted.

*Kernel.*—Form — Oval; Viable — yes; Length — 16.0 mm–19.0 mm; Taste — Bitter; Width — 12.0 mm–14.0 mm. Thickness — 5.0 mm–6.0 mm. Pellicle — Slight. Color When Mature — Light brown (RHS Greyed Orange 173 C).

*Use.*—The subject nectarine variety Burnectwo is considered to be a tree which produces fruit which mature in midseason and which are very firm, have an attractive coloration and are useful for both local and long distance shipping.

*Keeping quality.*—Excellent. Fruit has stored well up to 15 days after harvest at temperatures of about 1° C.

*Resistance to insects and disease.*—No particular susceptibilities were noted.

*Hardiness.*—No winter injury has been noted during the several years of evaluation in the Central San Joaquin Valley. The current variety has not been intentionally subjected to drought or heat stress and therefore this information is not available.

*Shipping quality.*—Well above average.

Although this new variety of nectarine tree possesses the described characteristics noted above, as a result of the growing conditions prevailing in the central part of the San Joaquin Valley of Central California, it is to be understood that variations of the usual magnitude and characteristics incident to changes in growing conditions, fertilization, pruning and pest control are to be expected.

Having thus described and illustrated our new variety of nectarine tree, what we claim as new and desire to secure by Plant Letters Patent is:

1. A new and distinct variety of nectarine tree substantially as illustrated and described and which is characterized as to novelty by producing an attractively colored clingstone nectarine, which is sufficiently matured for harvesting and shipment approximately July 1–July 8 under the prevailing ecological conditions experienced in the San Joaquin Valley of Central California.

* * * * *

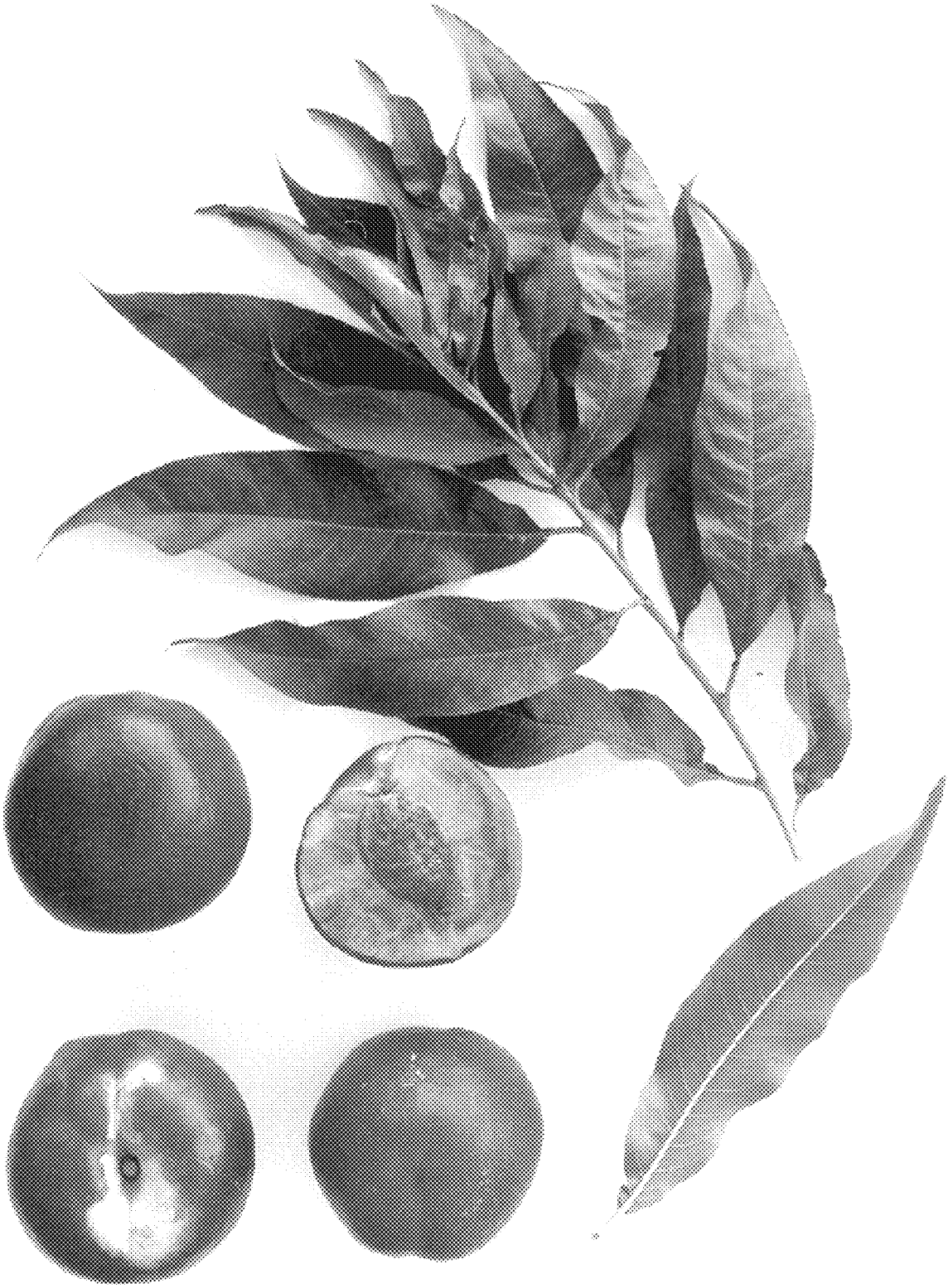

UNITED STATES PATENT AND TRADEMARK OFFICE

CERTIFICATE OF CORRECTION

PATENT NO. : PP 12,555 P2
DATED : April 16, 2002
INVENTOR(S) : John K. Slaughter et al.

It is certified that error appears in the above-identified patent and that said Letters Patent is hereby corrected as shown below:

Column 1,
Line 4, replace "'Burnetwo'" with -- 'Burnectwo' --.

Column 3,
Line 35, replace "tyical" with -- typical --.

Signed and Sealed this

Fourteenth Day of January, 2003

JAMES E. ROGAN
*Director of the United States Patent and Trademark Office*

UNITED STATES PATENT AND TRADEMARK OFFICE

CERTIFICATE OF CORRECTION

PATENT NO. : PP 12,555 P2
DATED : April 16, 2002
INVENTOR(S) : John K. Slaughter et al.

It is certified that error appears in the above-identified patent and that said Letters Patent is hereby corrected as shown below:

Column 4,
Under Flower Type, replace "showy type flower." with -- non-showy type flower. --.

Column 5,
Under Petal Size, replace "medium-large" with -- small --.
Under Petal Size; Length, replace "17 to 19" with -- 10-12 --.
Under Petal Size; Width, replace "15 to 18" with -- 9-11 --.
Under Petal Color, replace "69A; 67B; and 64B" with -- 45B --, respectively.
Under Petal Claw; Length, replace "1.5 to 2.1" with -- 3-6 --.
Under Petal Claw; Width, replace "1 millimeter." with -- 3-4 millimeters. --.
Under Petal Margins, replace "surface is smooth, but" with -- surface is smooth and entire, but --.
Under Floral Nectaries; Color, replace "Dull orange, to an orange gold color (approximately RHS Greyed Orange Group 168 B)." with -- Dull reddish orange, (approximately RHS Red Group 42 B). --.
Under Filaments, replace "approximately 14 to 16 millimeters." with -- approximately 12-14 millimeters. --.
Under Pistil, replace "Approximately 15 to 17 millimeters," with -- Approximately 14-16 millimeters, --.

Signed and Sealed this

Fifth Day of April, 2005

JON W. DUDAS
*Director of the United States Patent and Trademark Office*